United States Patent
Mir

(10) Patent No.: US 9,561,894 B2
(45) Date of Patent: Feb. 7, 2017

(54) ACTIVE COMPOUND FORMULATION PACKAGE AND ITS SUBSEQUENT RELEASE FOR USE ON PLANT AND PLANT PARTS

(71) Applicant: Nazir Mir, Somerset, NJ (US)

(72) Inventor: Nazir Mir, Somerset, NJ (US)

(73) Assignee: MirTech, Inc., Somerset, NJ (US)

(*) Notice: Subject to any disclaimer, the term of this patent is extended or adjusted under 35 U.S.C. 154(b) by 125 days.

(21) Appl. No.: 13/969,393

(22) Filed: Aug. 16, 2013

(65) Prior Publication Data

US 2014/0326620 A1 Nov. 6, 2014

Related U.S. Application Data

(60) Provisional application No. 61/819,633, filed on May 5, 2013.

(51) Int. Cl.
| | |
|---|---|
| *B65D 81/28* | (2006.01) |
| *A01N 27/00* | (2006.01) |
| *A01N 25/06* | (2006.01) |
| *B65D 81/26* | (2006.01) |
| *A01N 25/22* | (2006.01) |

(52) U.S. Cl.
CPC .............. *B65D 81/28* (2013.01); *A01N 25/06* (2013.01); *A01N 25/22* (2013.01); *A01N 27/00* (2013.01); *B65D 81/26* (2013.01)

(58) Field of Classification Search
CPC ........ A01N 25/22; A01N 27/00; A01N 25/04; A01N 25/14; A01N 25/28; A01N 2300/00; A01N 25/06; B65D 81/26; B65D 81/28
See application file for complete search history.

(56) References Cited

U.S. PATENT DOCUMENTS

| | | | | |
|---|---|---|---|---|
| 2002/0127305 A1* | 9/2002 | Clarke | .................. | A23B 7/148 426/106 |
| 2002/0198107 A1* | 12/2002 | Kostansek | .................... | 504/209 |
| 2004/0170780 A1* | 9/2004 | Giraud | ......................... | 428/34.1 |
| 2005/0250649 A1* | 11/2005 | Jacobson | ............... | A01N 27/00 504/357 |
| 2006/0154822 A1* | 7/2006 | Toivonen | ............... | A01N 27/00 504/117 |
| 2009/0088323 A1 | 4/2009 | Basel et al. | | |
| 2013/0004634 A1* | 1/2013 | MCcaskey et al. | ......... | 426/316 |

FOREIGN PATENT DOCUMENTS

| | | | |
|---|---|---|---|
| EP | 1 192 858 | | 4/2002 |
| EP | 1 593 306 | | 11/2005 |
| JP | 2012/0256987 | * | 3/2012 |
| WO | WO 2006/072180 | | 7/2006 |
| WO | WO 2008/089140 | | 7/2008 |

OTHER PUBLICATIONS

Hayashi et al., JP 2012/00256987, published: Mar. 22, 2012, English Machine Translation obtained on May 21, 2015.*

* cited by examiner

*Primary Examiner* — Ali Soroush
*Assistant Examiner* — Genevieve S Alley
(74) *Attorney, Agent, or Firm* — Klarquist Sparkman, LLP

(57) ABSTRACT

A package for storing or containing at least one ethylene response manipulation agent such as 1-methylcyclopropene is disclosed. The package can have multiple film layers, but preferably the outer layer comprises a polymer at least partially soluble when contacted with an aqueous media, and the inner layer comprising an ethylene response manipulation agent permeable film structure. Aerosols comprising the ethylene response manipulation agents are also disclosed.

20 Claims, 7 Drawing Sheets

Figure 1:
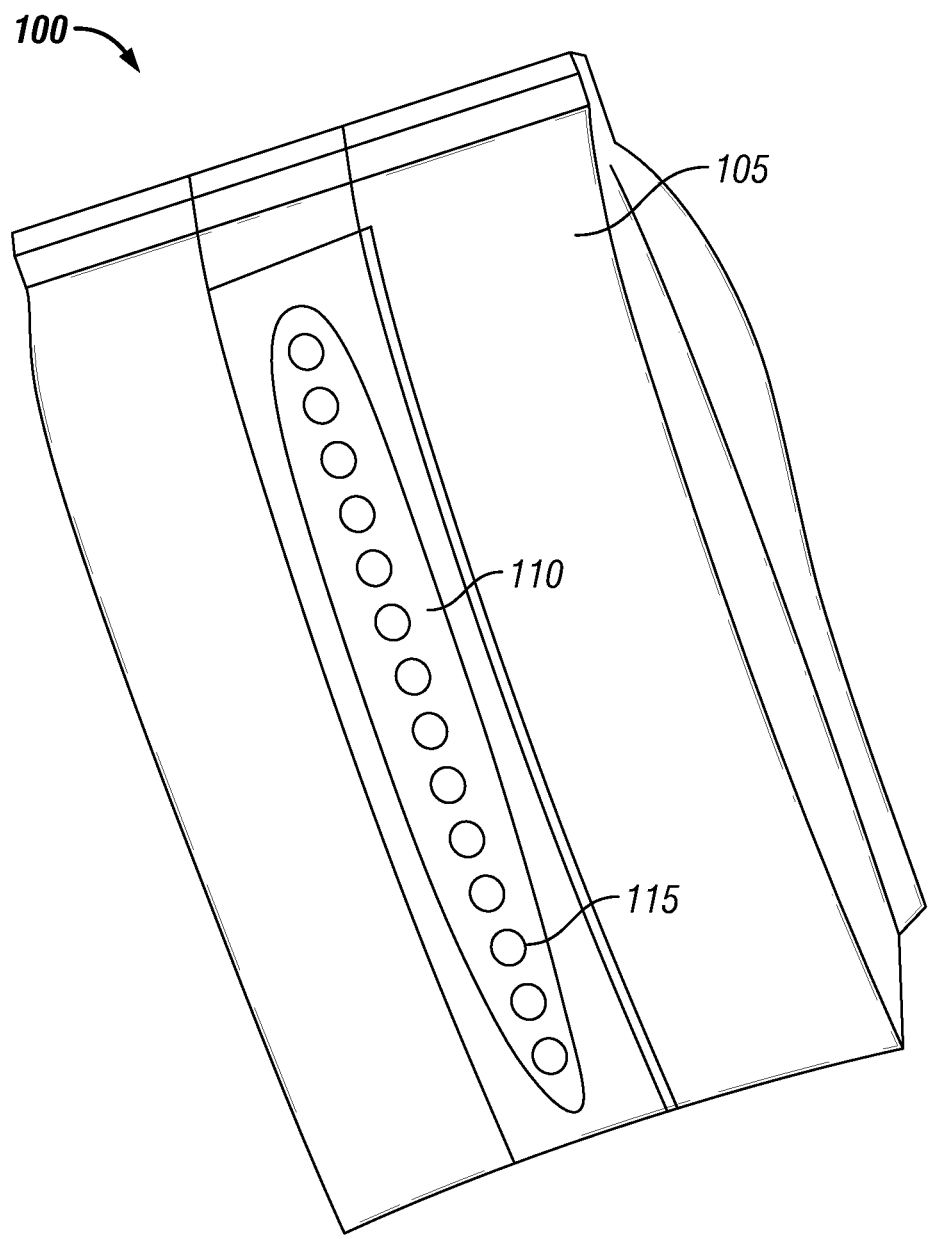

ACTIVE COMPOUND FORMULATION PACKAGE AND ITS SUBSEQUENT RELEASE FOR USE ON PLANT AND PLANT PARTS

RELATED APPLICATIONS

This application is related to and claims priority from U.S. Provisional Patent Application Ser. No. 61/819,633 filed May 5, 2013, the disclosure of which is incorporated herein by reference. This application is also related to U.S. application Ser. No. 13/922,122 filed Jun. 19, 2013, the disclosure of which is incorporated herein by reference.

BACKGROUND OF THE INVENTION

Volatile active compounds such as ethylene response manipulation agents or plant disease and insect controlling materials or other plant growth regulating materials are dispersed in water based mediums to either directly apply to intended plant or plant parts as liquid solution or use water based medium to release bioactive gas from encapsulated matrix to allow gaseous exposure of bioactive compound to intended plant or plant parts under closed environments.

These compounds are mostly manufactured in concentrated and generally stable forms by either encapsulation process, or forming salts or conjugated complexes for storage and distribution. The product in powder or tablet form is packed in water impermeable packaging which is cut open before use, contents transferred into another container containing water based medium to release MCP gas for gaseous exposure under leak proof conditions. This process is complicated and limits the use of the bioactive volatiles to only storage environments that are properly sealed. There is a heartfelt need in the industry to develop a storage and control release package for encapsulated bioactive materials so that the scope of the technology can be extended to benefit produce industry under transit, retail and consumer conditions.

The disclosed invention provides a package for storing and control release volatile active compounds from its solid or liquid formulations which comprise of at least portion of encapsulated, conjugated or salts of bioactive compound. The bioactive compound package incorporates volatile compound, water and gas permeable portions which may include perforations that are sealed with peelable adhesive, water soluble barrier layer or photosensitive polymer barrier layer. A method to ensure complete release of volatile compounds from their encapsulated formulations is provided so that the packaging materials can either be recycled or discarded as non-hazardous waste material.

SUMMARY OF THE INVENTION

In one aspect of the invention, a package for storing or containing at least one ethylene response manipulation agent is disclosed. The package can comprise at least 2, and up to 9, film layers; one film layer comprising an inner layer, and at least one other layer comprising an outer layer. The outer layer can comprise a polymer at least partially soluble when contacted with an aqueous media, and the inner layer can comprise an ethylene response manipulation agent permeable film structure. Preferably, the ethylene response manipulation agent, especially 1-methylcyclopropene, is at least partially encapsulated. The partial encapsulation can comprise at least 0.1 percent and up to about 10 percent, preferably up to 5 percent, by weight of the ethylene response manipulation agent. Preferably the encapsulant is cyclodextrin or a cyclodextrin derivative. The ethylene response manipulation agent can be selected from the group consisting of cyclopropene, cyclopropene conjugates, cyclopropene salts or cyclopropene encapsulating materials, but preferably is 1-methylcyclopropene.

The package can be in different forms, but is preferably a sachet or a pad, especially when placed in a storage, transit or food container such that release of the ethylene response manipulation agent is controlled into an environment.

The inner film layer of the package preferably comprises perforations, especially wherein the perforations have a mean diameter from 40 micrometers to 900 micrometers. The inner film layer of the package can also comprise microporous film, spun-bonded (or spunlaced, or carded and bonded fibers, or melt spun) olefin (such as ethylene or propylene polymers and copolymers), waxed paper, non-woven polyester, or non-woven nylon, including mixtures of these fabrics and fibers.

The outer film layer of the package can also comprise a coating material, preferably with a thickness of 1 to 50 μm.

The package can further store or contain a polyol liquid medium, or a hydrogel medium, or a combination of polyol and hydrogel medium, wherein particles comprising the ethylene response manipulation agent are dispersed in said medium. The package can also further store or contain water absorbing or adsorbing materials.

In another embodiment, the invention is a package for storing or containing at least one ethylene response manipulation agent, preferably 1-methylcyclopropene, the package comprising at least 2 film layers, one film layer comprising an inner layer, and at least one other layer comprising an outer layer, wherein the outer layer comprises a polymer at least partially degradable when exposed to light, and the inner layer comprises volatile ethylene response manipulation agent permeable film structure. MCP permeable structure.

In any embodiment, the inner film layer can have an ethylene response manipulation agent (especially 1-methylcyclopropene) transmission rate, FL-1, at 23° C. of 500 to 250,000 cm3/(m2-day). Also in any embodiment, the inner film layer has a moisture transmission rate, FL-1, at 37.8 C of 10 to 500 cm3/(m2-day).

The outer film layer of any embodiment can further comprise water absorbing or adsorbing materials. The water absorbing or adsorbing materials, either in the film layer or contained within the package, are preferably selected from the group consisting of polyacrylate based super absorbent polymers, calcium chloride, clay, starch, and silica gel.

In a third embodiment, the invention is an aerosol comprising at least one partially encapsulated ethylene response manipulation agent, preferably wherein the partial encapsulation comprises at least 0.1 percent and up to about 10 percent by weight of the ethylene response manipulation agent; at least one polyol liquid medium, or a hydrogel medium, or a combination of polyol and hydrogel medium, wherein particles comprising the ethylene response manipulation agent are dispersed or mixed in said medium; and at least one propellant. The ethylene response manipulation agent of the aerosol can be selected from the group consisting of cyclopropene, cyclopropene conjugates, cyclopropene salts or cyclopropene encapsulating materials, preferably 1-methylcyclopropene. The propellent can be selected from the group consisting of compressed air, inert gases, volatile hydrocarbons, ethers, and hydro fluorocarbons.

Partially encapsulated or volatile antimicrobials which may include chlorine dioxide, sulphur dioxide, thymol, carvacrol, cinnamaldehyde, allyl isothiocyanate, ethanol, oregano extracts and other synthetic or natural occurring flavanols, phenolic compounds or organic acids or Hydrogen Peroxide can be added to the formulation for aerosol application.

In a fourth embodiment, the invention is a multilayer film structure, preferably 2 to 9 layer film structure, formed into a package for storing and containing an ethylene response manipulation agent, such as 1-methycyclopropene, and controlling its release into an environment. This controlled release is accomplished by selecting an outer film layer of the film structure to be at least partially water soluble, or at least partially light degradable, and by having both inner and outer film layers (at a minimum) enabled with porosity to enable the volatile ethylene response manipulation agent (such as 1-MCP, preferably encapsulated) capable of migrating though the film structure of the package and into an exterior environment.

BRIEF DESCRIPTION OF THE FIGURES

FIG. 1 is an isometric illustration of a packaging device including a plurality of micro-perforations in inner film layer which are covered by an exterior water soluble film layer in accordance with an exemplary embodiment of the present invention.

FIG. 2 is an illustration of Vertical Form-Fill-Seal (VFFS) equipment creating a bioactive compound package in accordance with the prior art.

FIG. 3 is an isometric illustration of a packaging device containing multiple invention packs in large water vapor impermeable pack. At the time of bioactive compound application, the exterior large bag is cut open; the invention packs are removed and placed in individual produce boxes varying in weight from 3 to 50 lbs.

FIG. 4 is an isometric illustration of a packaging device containing multiple invention packs in large water vapor impermeable Ziplock™ pack. At the time of bioactive compound application, the exterior large Ziplock bag is opened, the invention packs are removed and placed in individual produce boxes varying in weight from 3 to 50 lbs.

FIG. 5 is an illustration of a roll stock containing one perforated film layer. Perforations are coated with water soluble adhesive or bonded to water soluble film layer in accordance with an exemplary embodiment of the present invention.

FIG. 6 is an illustration of the lid stock comprising inner water vapor and 1-MCP gas permeable film layer bonded or sealed to peelable exterior film layer. The inner permeable film layer (6A) or inner perforated film layer (6B) is connected with and sealing the tray containing partially encapsulated bioactive compound formulation.

FIG. 7 is an illustration of retail and consumer canister containing partially encapsulated bioactive compound formulation constructed in accordance with the prior art.

DETAILED DESCRIPTION OF THE INVENTION

A storage and control release package for ethylene response manipulation agents include ethylene analogues such as propylene, acetylene, carbon monoxide, 1-butene, etc.; Ethylene releasing compounds such as 2-(chloroethyl) phosphonic acid [an example of commercial name is Etheral], 2-(chloroethylmethyl)bis(phenylmethoxy) silane [commercial name is Silaid], 2-(chloroethyl)tris(2-methoxyethoxy) Silane [an example of commercial name is Alsol]; Ethylene synthesis inhibitors such as aminoethoxyvinylglycine (AVG) [an example of commercial name is RETAIN], aminooxyacetic acid (AOA); and Ethylene action inhibitors such as Silver ions, 2,5-norbornadiene (NBD) and 1-methylcyclopropene.

While the invention discloses packaging for formulations comprising of encapsulated 1-MCP, a person with ordinary skill and art can use the invention for other control release ethylene manipulation agents as listed above or other chemicals of agricultural importance. For instance the disclosed invention may be applied to package partially encapsulated or volatile antimicrobials which may include chlorine dioxide, sulphur dioxide, thymol, carvacrol, cinnamaldehyde, allyl isothiocyanate, ethanol, oregano extracts and other synthetic or natural occurring flavanols, phenolic compounds or organic acids or Hydrogen Peroxide. One aspect of this invention may be to package formulations that may contain at least one fungicide, insecticide or biopesticide, antioxidants such as diphenylamine, ethoxyquin, etc., plant growth regulators such as Gibberellic Acid (GA3), Etheral, aminoethoxyvinylglycine (AVG), etc. or mixtures of these in addition to encapsulated ethylene response manipulation agents such as 1-MCP for application of plants or plant parts such as fruit, vegetable, flowers and field crops.

The packaging device provides a web for at least partially encompassing encapsulated ethylene effect modifier mixture within which may be in solid, liquid or a combination thereof form, that may be constructed using one or more polymeric base films and in various configurations. For example, the web may be constructed as a bag, lid stock, stand-up pouch, and the like. It is contemplated that the base films may be any one of or combination of polymer groups such as polyalkenes (e.g., polyethylene—low density, linear low density, high density, metallocene polyethylene, etc.), polyvinyls (e.g., polypropelene), polystyrenes (e.g., polyvinyl chloride), polysiloxanes (e.g., silicone rubber), and polydiens (e.g., natural rubber), compostable polymers such as polylactic acid (PLA), Polycaprolactone (PCL) and Polyvinyl Alcohol (PVA) or gelatin. Further, the base films may be extruded from a single polymer or blends of various polymers where each polymer performs a specific function, such as contributing strength, transparency, sealability, or machinability, to meet specific product requirements. Similarly, the material(s) of the base film may be processed using various technologies and treatment applications, such as lamination, to provide the packaging device with specific properties and for achieving particular configurations.

In one embodiment, the package comprises various base film layers of similar or different film materials which are bonded together through lamination, adhesive coating or heat sealing. The bonding or coating material may contain pressure or temperature sensitive materials. One or all the layers may be made up of water soluble materials such as Ethylene vinyl Alcohol (EVOH) or photodegradable material such as Ethylene carbon monoxide.

In another embodiment, the inner film layer may be perforated flexible film bonded or adhered to the outer film layer comprising of water soluble or photodegradable polymers such that when the package is exposed to moisture or high relative humidity environment or light, the outer film layer will solubilize or degrade, and covered perforation open such that water vapor or free water can enter the package in a controlled manner, hydrate the encapsulated 1-MCP matrix thus leading to 1-MCP release from the package. One such application of this invention may be to release MCP under transit and handling conditions.

In another embodiment, the inner film layer may be made from spun-bonded olefin such as Tyvek available from DuPont, microporous films with a pore size of 5 to 300μ, waxed paper or non woven nylon, polyethylene, polypropylene, etc. which are coated or adhered to the outer film layer generally in the range of 1 to 50μ thickness and comprising of water soluble or photodegradable polymers such that when the package is exposed to moisture or high relative humidity environment or light, the outer film layer will solubilize or degrade, and covered pores or open spaces in the inner layer open such that water vapor or free water can enter the package in a controlled manner, hydrate the encapsulated 1-MCP matrix thus leading to 1-MCP release from the package. One such application of this invention may be to release MCP under transit or storage conditions.

In another embodiment, the formulation comprising of at least one ethylene response manipulation agent which is at least partially encapsulated, a polyol liquid medium, or a hydrogel medium, or a combination of polyol and hydrogel medium, wherein particles are dispersed in said medium, wherein said ethylene response manipulation agent comprises cyclopropene, cyclopropene conjugates, cyclopropene salts or cyclopropene encapsulating materials is mixed with other coating materials and then applied on the inner surface of the single MCP permeable layer or the formulation coating can be sandwiched between 2 or more film layers, the film layer or layers that form the outer surface of the package, at least one of those layers is impermeable to MCP so that when MCP is activated it can only migrate into the package.

In a preferred embodiment shown in FIG. 1, a storage device 100 is a bag configuration using heat sensitive polymeric base film layers bonded (i.e., laminated) together, which further provide a transmission system for water or water vapor to enter the package and subsequently allow the MCP exit the package on hydration of encapsulated formulation. Thus, it is understood that the packaging device 100 includes gas and water permeable properties which allow it to be used for the distributing, storing and releasing of MCP in a controlled fashion. In the current embodiment, the packaging device 100 includes a perforated 115 first base film 105, which is made from a cast polypropylene (CPP) that is bonded (laminated) to a second base film 110, which is made from an Ethylene vinyl Alcohol (EVOH). It is to be understood that the first and second base film may be constructed from various materials, such as those previously mentioned. The first base film 105 may be constructed generally in a standard bag configuration. For instance, the first base film 105 may provide a web where the sidewall is constructed from connecting the ends of a continuous piece of material, thereby constructing opposing sidewalls of a bag. Further, the top and bottom edges may be joined together and may include gusseting. This connection of the continuous piece of material and joining of the edge(s) provides the bag with an outer surface exposed to an exterior (ambient, relatively high in Relative Humidity) environment and an inner surface which defines an interior space (Relatively low in Relative Humidity) allowing for the storage of encapsulated formulation within and between the opposing sides of the inner surface. From Example 1, described below, the packaging device 100 or "bag" may be one hundred twenty one millimeters (121 mm) wide with additional gusset width of approximately thirty-seven millimeters (37 mm) on each side and three hundred fifty millimeters (350 mm) long. Other dimensional specifications for a water, water vapor and MCP gas capable packaging device may be employed as contemplated by those of ordinary skill in the art. The second base film 110 may be constructed in the configuration of a "strip" of material or around the entire surface of the base film 105. The strip may have certain dimensional characteristics which allow it to be connected with the first base film in such a manner that it provides an integral overall appearance. For instance, the strip may be one-quarter inch (¼") wide and have a length which corresponds to the length of the first base film 105. It is to be understood that the dimensional characteristics of the strip may vary without departing from the scope and spirit of the present invention. For instance, the strip may include a pre-determined length that is equivalent to or shorter than the length of the first base film 105 and may have a width less than or greater than one-quarter inch wide or width or length matching exactly the width and length of base film 105.

It is useful to characterize the inherent moisture transmission characteristics of an inner layer polymeric film or portion thereof. By "inherent" it is meant the properties of the film itself, in the absence of any perforations or other alterations. It is useful to characterize the composition of a film by characterizing the moisture transmission characteristics of a film that has that composition and that is 25.4 micrometers thick. It is contemplated that, if a film of interest were made and tested at a thickness that was different from 25.4 micrometers (e.g., from 8 to 76.2 micrometers), it would be easy for a person of ordinary skill to accurately calculate the moisture transmission characteristics of a film having the same composition and having thickness of 25.4 micrometers or 1 mil. The moisture transmission rate of a film having thickness 25.4 micrometers is labeled "FL-1" herein.

Preferred are film compositions for which the FL-1 for 1-MCP transmission at 23° C., in units of $cm^3/(m^2\text{-day})$, is 500 or higher; more preferred is 5,000 or higher; more preferred is 10,000 or higher; more preferred is 20,000 or higher; more preferred is 30,000 or higher. Preferred are films with FL-1 for 1-MCP transmission at 23° C., in units of $cm^3/(m^2\text{-day})$, of 250,000 or lower; more preferred is 150,000 or lower; more preferred is 100,000 or lower.

Preferred are films with FL-1 for water vapor at 37.8° C., in units of $g/(m^2\text{-day})$, of 10 or higher; more preferred is 20 or higher. Preferred are films with FL-1 for water vapor at 37.8° C., in units of $g/(m^2\text{-day})$, of 500 or lower; more preferred is 300 or lower; more preferred is 250 or lower.

In preferred embodiments, some or the entire interior and exterior surface of the enclosure of the present invention is polymeric. Preferably, the polymer is in the form of a polymeric film or coating. Preferred polymeric film or coating layers have an average thickness of 1 micrometer or more; more preferably 2 micrometer or more; more preferably 5 micrometer or more. Independently, some suitable polymeric film or coating layers have an average thickness of 50 micrometers or less; more preferably 40 micrometer or less; more preferably 30 micrometer or less; more preferably 25 micrometer or less.

Preferably, inner layer polymeric film is used that has perforations. Preferably, the holes have mean diameter of 40 micrometers to 900 micrometers. Preferably, the holes have mean diameter of 50 micrometers or more; more preferably 75 micrometers or more; even more preferably 100 micrometers or more; most preferably 150 micrometers or more. Independently, preferably, the holes have mean diameter 900 micrometers or less; more preferably 700 micrometers or less. If a hole is not circular, the diameter of the hole is considered herein to be the diameter of an imaginary circle that has the same area as the actual hole.

Preferably, the percentage of holes that fall within the above described specification is 10% or more (by volume of hole numbers); more preferably 20% or more; more preferably 30% or more. In an independent embodiment, preferably, the percentage of holes that fall within the above describe specification is 100% or less; more preferably 95% or less; more preferably 90% or less.

In preferred embodiments, the number of holes in the enclosure is 1 or more; more preferably 5 or more; more preferably 10 or more. In preferred embodiments, the number of holes in the enclosure is 200 or fewer; more preferably 150 or fewer; more preferably 100 or fewer.

Holes in polymeric film may be made by any method. Suitable methods include, for example, laser perforation, hot needles, flame, low-energy electrical discharge, and high-energy electrical discharge. One preferred method is laser perforation. Among embodiments in which laser perforation is used, it is preferred to design or select polymeric film that is well suited to laser perforation. That is, the polymeric film is designed or selected so that the laser easily makes holes that are round and have predictable size. Preferred laser is a carbon dioxide laser. For different polymeric film compositions, the appropriate wavelength of laser light may be chosen. For polymeric films that contain polypropylene and/or copolymers of polypropylene with one or more polar monomer, it is preferred to choose a carbon dioxide laser producing infrared light that includes infrared light of wavelength 9.25 micrometer.

Figure 2:
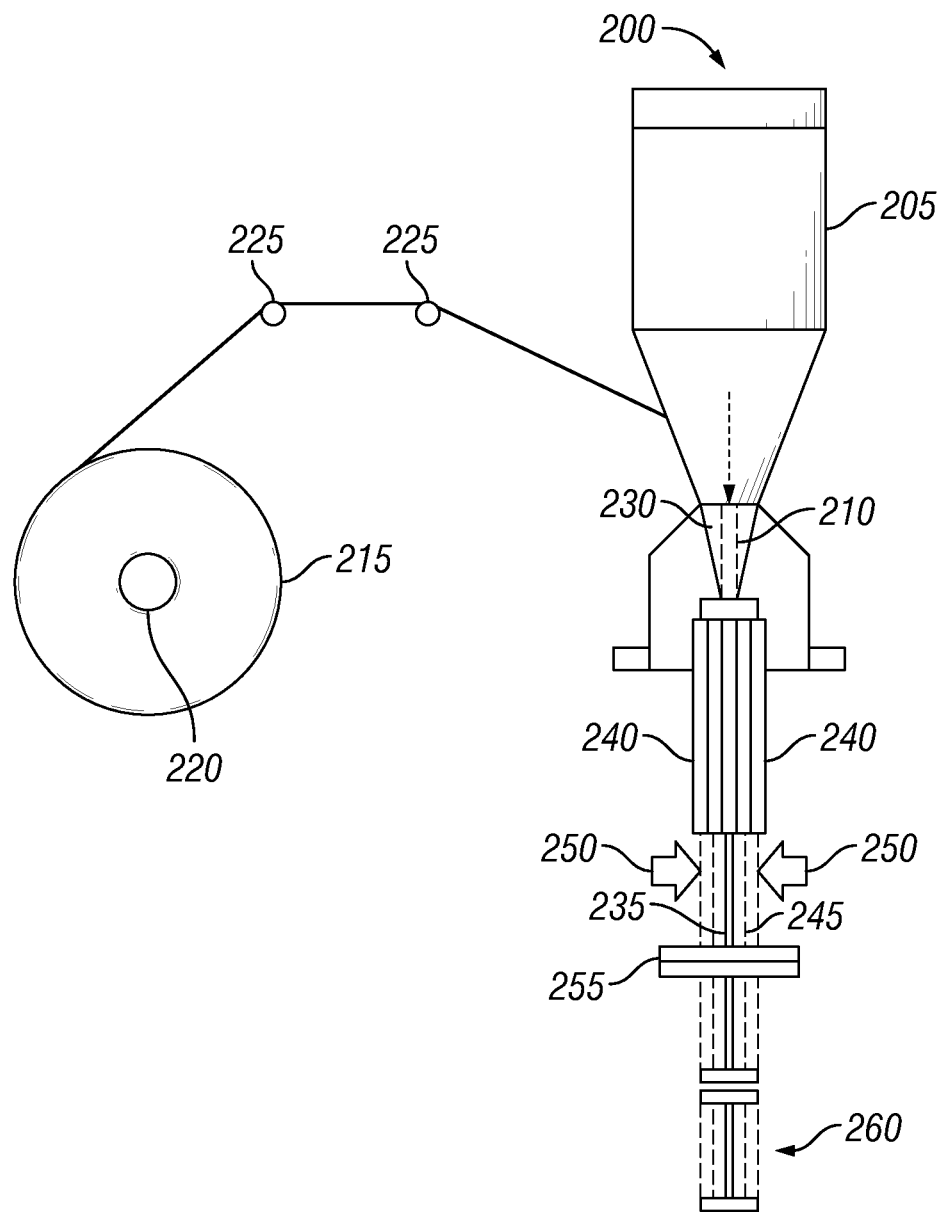

FIG. 2 illustrates Vertical Form-Fill-Seal equipment to create a package, in accordance with prior art. The vertical form-fill-seal equipment 200 is used widely for filling packaging products such as food, agricultural and consumer products. The equipment 200 comprises a feed hopper or funnel 205 for receiving the material to be packed, which may include 1-MCP encapsulated powder or other antimicrobial powder or biocide powder. The material is then metered to get the quantity needed for a single package after which they move through the filling tube 210. The equipment 200 also has packaging film roll 215 fed on a roller 220. The film 215 is moved through series of rollers 225 to provide tension and wrapped around a tube 230, which continues from the feed hopper or funnel 205. Vertical seams 235 are formed when the film is wrapped around 230 and the seal is joined together using for example a vertical sealing unit 240, which utilizes heat, pressure and time to help join. Once sealed the result would be a long hollow tube 245. The tube may be gusseted using an available gusseting mechanism 250. The long hollow tube 245 is then joined together using for example a horizontal sealing unit 255, which utilizes heat, pressure and time to help join. The time when the bottom seal is made, the metered material, to be packed, drops from feed hopper 205 to the filling tube 210, into the hollow tube 245 that is sealed in the bottom. Once the hollow tube is filled with the material, it drops down to a certain distance and a second seal is made on the top using the horizontal sealer 255. The horizontal sealing machine 255 makes two seals close to each other, where in one seal would be the top seal of package 1 filled with material and the other would be bottom seal of package 2 that needs to be filled with material. A cutting blade, not shown in the figure, makes a cut right in the middle of the two seals, making the package 260 complete and separated from the hollow tube 245.

Figure 3:
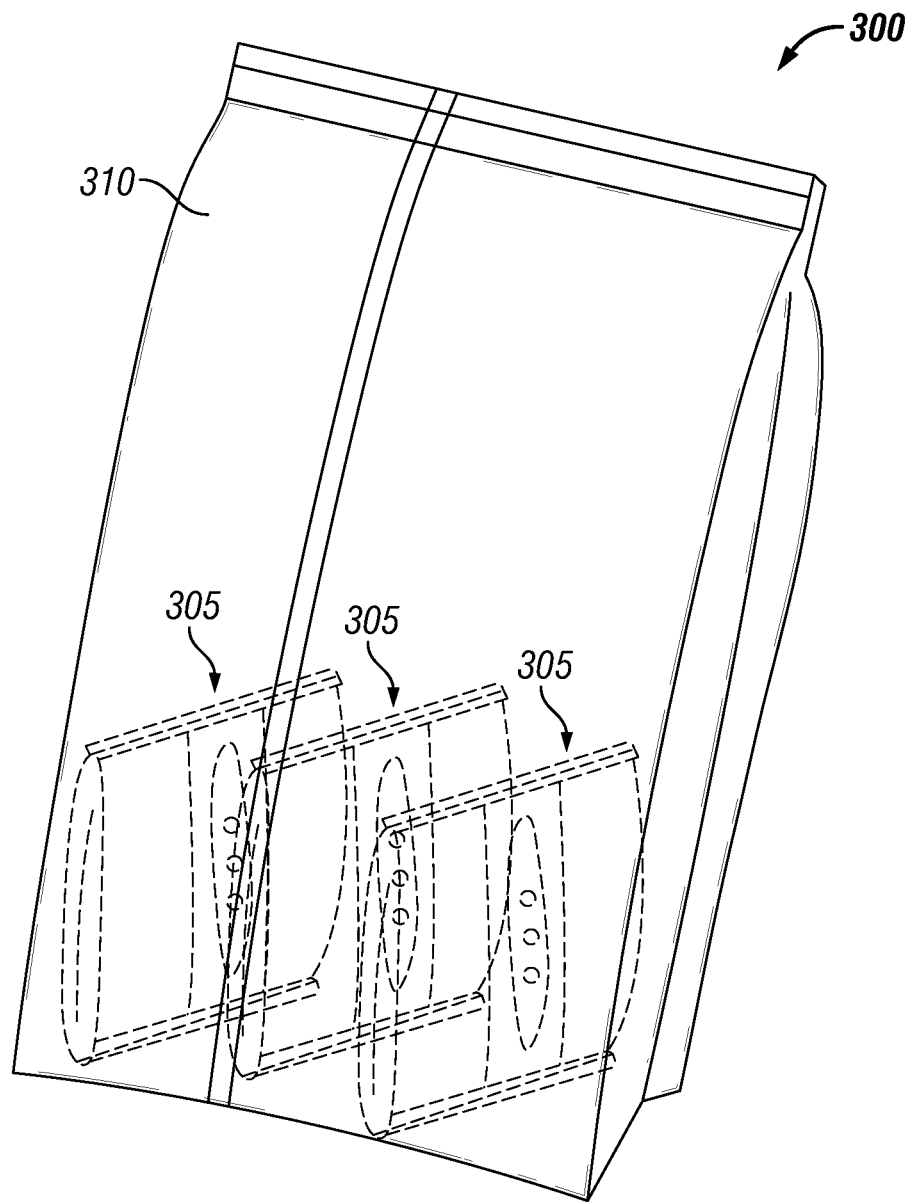

Fruit and vegetables are transported in large trucks or containers which contain products in cardboard boxes or crates which generally contain 3 to 50 lb each. There is a need to develop a storage and control release package for individual box or pallet treatment. For definition a pallet is a column of individually boxed produce on a truck or container for shipment. A standard container has 20 pallets numbering 48 boxes per pallet, each weighing approximately 40 lbs or 960 boxes per container. There is an industry need to develop small storage and control release packages for individual box treatment. Therefore, in another package embodiment 300 shown in FIG. 3, multiple small storage and control release packages 305 manufactured as described in FIG. 1 and containing at least partially encapsulated volatile compounds such as 1-MCP, are packed in a non-perforated flexible bag 310 which is heat sealed on the sides for storage of multiple invention packs 305 in a large pack 310. At the time of packing, the large pack 310 is cut open, individual small storage and control release packages 305 are individually placed into one or multiple packages per produce box and then boxes are palletized and loaded for shipment. During transit, the respiration of the produce leads to water evolution and a high humidity environment around the package 305 is created which solubilizes the outer layer and opens the perforations on the inner layer. The water vapor can now enter the package 305, hydrate encapsulated materials of package 305 and release 1-MCP for minimizing the deleterious effects of ethylene gas on produce. The control release package 305 may be constructed from mono or multiple film layer structure, the perforations of which may not be covered as multiple packs are placed in a outer pack 310 which is impermeable to gas and moisture.

Figure 4:
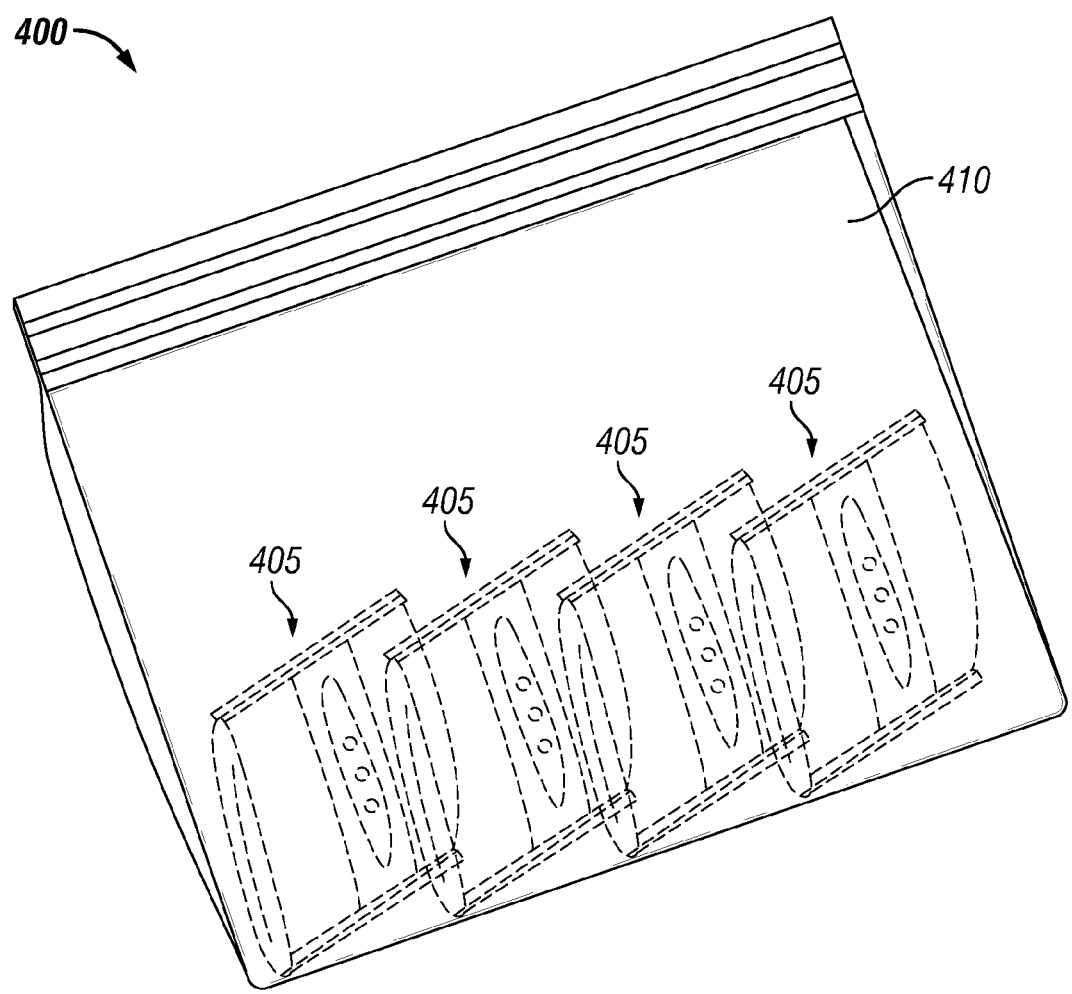

In another embodiment 400 shown in FIG. 4, multiple small storage and control release packages 405 manufactured as described in FIG. 1 and containing at least partially encapsulated volatile compounds such as 1-MCP, are packed in a non-perforated flexible Ziplock™ (Trademark of SC Johnson) bag 410 having 3 sidewalls and a Ziplock for closing the bag 410. At the time of packing, the Ziplock on the large pack 410 is opened, individual small storage and control release packages 405 are individually placed into one or multiple packages per produce box and then boxes are palletized and loaded for shipment. During transit, the respiration of the produce leads to water evolution and a high humidity environment around the package 405 is created which solubilizes the outer layer of package 405 and opens the perforations on the inner layer of package 405. The water vapor can now enter the package 405, hydrate encapsulated materials of package 405 and release 1-MCP for produce treatment. The control release package 405 may be constructed from mono or multiple film layer structure, the perforations of which may not covered as multiple packs are placed in a outer Ziplock bag 410 which is impermeable to gas and moisture.

Figure 5:
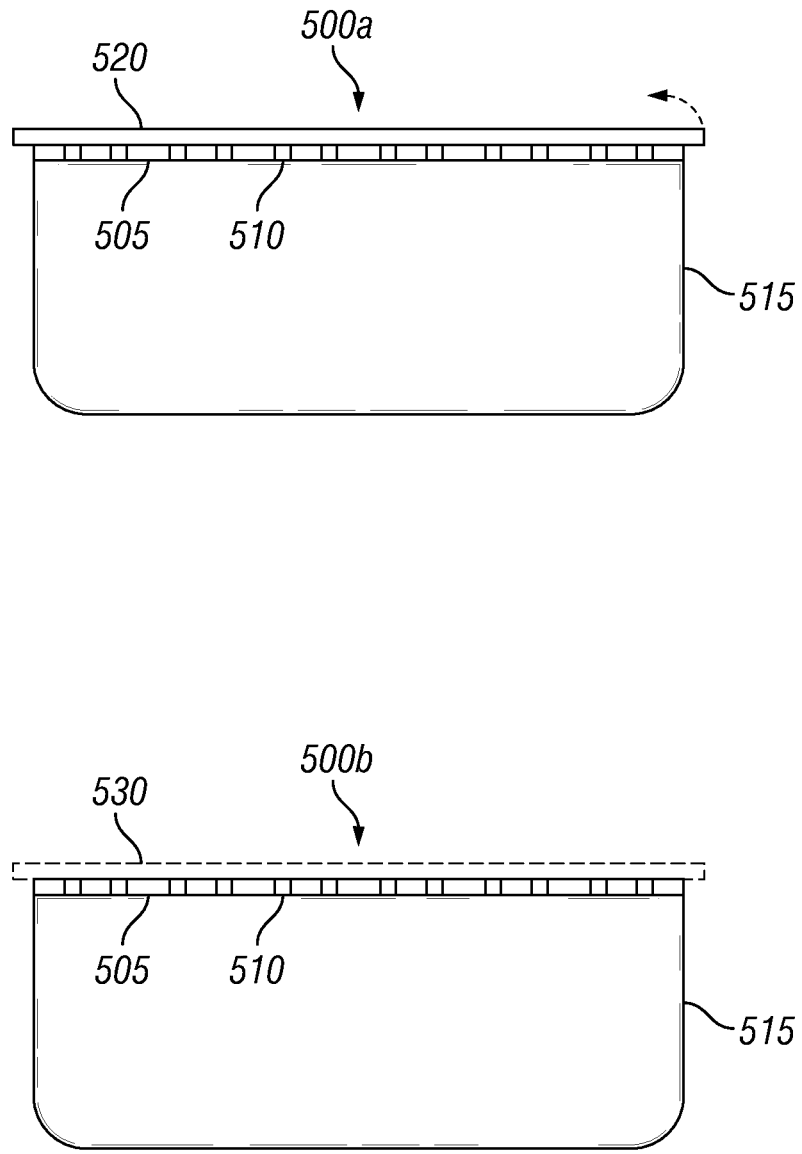
Figure 6:
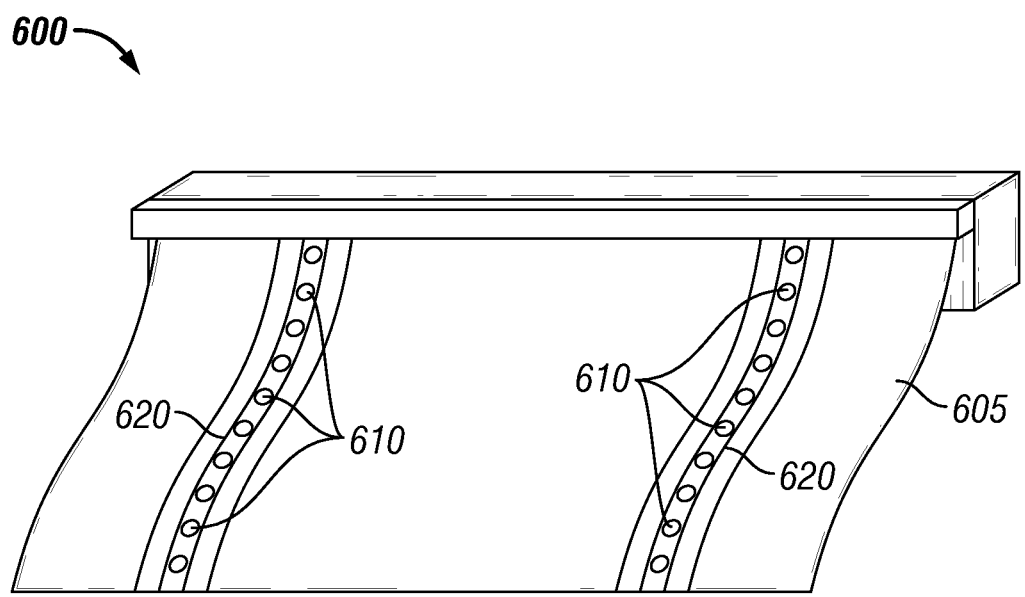

Referring now to FIGS. 5 and 6, the storage and control release packaging device is constructed as a lid stock 500a or 500b including a first base film 505. In a preferred embodiment, the first base film 505 is a transparent polypropylene for connection with a tray 515. The first base film 505 further includes a plurality of micro-perforations 510 that extend through the first base film 505. The micro-perforations 510 of first base film are either covered with peelable second base film 520 as in 500a or water soluble second base film 530 as in 500b. In the current embodiment, the lid stock 500a or 500b is generally configured as a transparent film which connects with and seals the tray creating a closed interior atmosphere. It is to be understood that the lid stock 500a or 500b may be constructed from any of the various materials identified previously and include various structural properties, such as being transparent, translucent, opaque, and the like, and having various rigidity characteristics. The lid stock 500a or 500b is capable of being constructed to provide proper sealing of variously configured trays and the like. Thus, the lid stock 500a or 500b may be constructed in a pre-determined pattern to successfully engage with a specific tray having certain dimensions.

In FIG. 6, the packaging device is shown alternatively constructed as a roll stock 600 including a base film 605. It is contemplated that the roll stock 600 may be any of the numerous plastic wraps currently available that are modified to include the covered or coated micro-perforations 610 and provide the user the ability to determine overall roll stock 600 length for engagement with various trays. The roll stock 600 also includes a water soluble layer 620 covering or coating plurality of micro-perforations 610 which allow it to provide a proper internal atmosphere when the roll stock 600 is sealed with a tray. It is contemplated that the lid stock 500a or 500b and/or roll stock 600 may be variously configured, such as in various polygonal configurations like a generally square shape, rectangular shape, diamond shape, and the like, or other configurations, such as an conical shape, oval shape, and the like, for connection with a tray in establishing an inner storage space. Alternatively, the disclosed invention may be constructed as a stand-up pouch, fold over flap pouch or in other packaging formats in accordance with the prior art.

The lid stock film as described above may be used to construct a bioactive compound release pad which can placed at the bottom of the food package. The moisture released from the food can enter the pad, release 1-MCP gradually which in turn will be forced to get out from the pad and interact with packaged food thereby help in extending its shelf life. Similarly the film may be used to construct sticky labels which can be used to release 1-MCP in a controlled manner.

Microwave absorbent materials commonly known as susceptors can be added to the packaging film to help in releasing any residual 1-MCP from the encapsulation matrix post application. Such susceptors for reference may include one or combination of the ferrites, metal oxides, salt hydrates, and titanium nitride or commercially available metallized film susceptor. The major purpose of this process would be to use microwave energy to generate enough heat and pressure that would ensure complete release of MCP from the encapsulation matrix so that the container contents including encapsulated packaging materials can be trashed as non-hazardous waste. The temperatures required to release 1-MCP completely from encapsulated matrix generally would be in the range of 100° C. or higher, more preferably, 110° C. or higher, more preferably 115° C. or higher. More preferably the package temperatures would be 250° C. or lower, more preferably 220° C. or lower, more preferably 200° C. or lower. The pressure required to release 1-MCP completely from encapsulated matrix generally, would be in the range of 5 millibars or higher, more preferably, 10 millibars or higher, more preferably 15 millibars or higher. More preferably the required pressure would be 400 millibars or lower, more preferably 300 millibars or lower, more preferably 100 millibars or lower. Although the temperature and pressure ranges are shown by example, other techniques or alterations can be made by a person of ordinary skill and art to aid in the release of 1-MCP from the encapsulating matrix.

Figure 7:
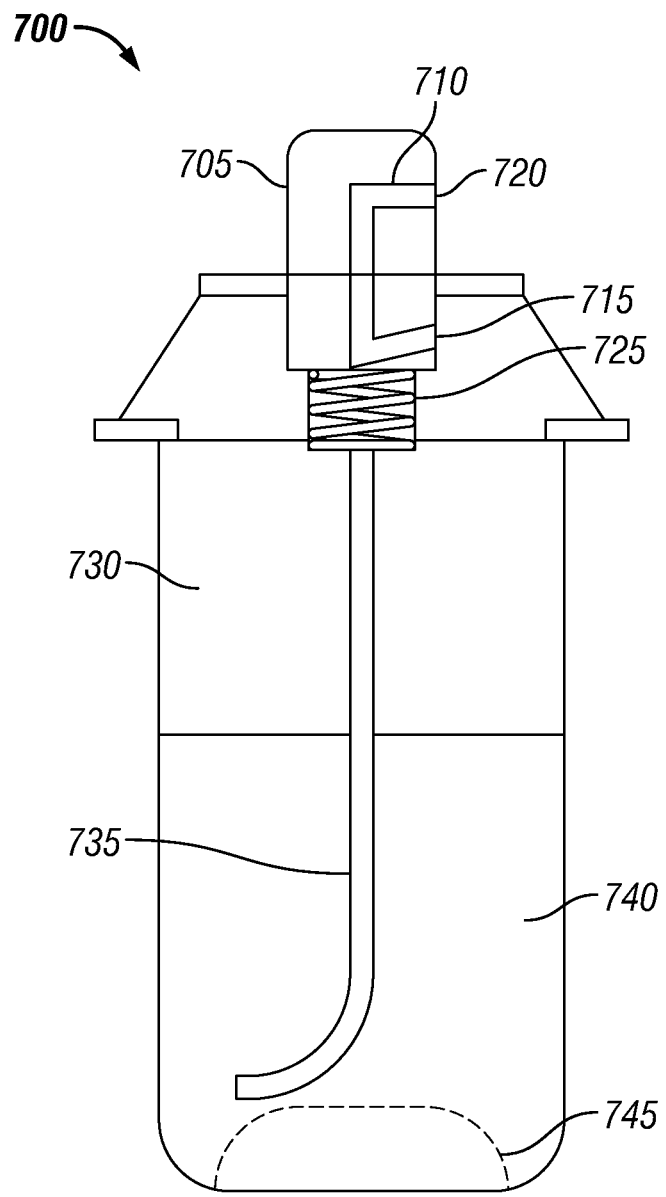

FIG. 7 illustrates an aerosol spray can to disperse a liquid product, in accordance with prior art. The aerosol spray can 700 contains a depressible head 705 and a narrow channel 710 running inside the depressible head. One side of the channel is the nozzle 720 that helps atomize the liquid product 740 inside the aerosol spray can 700 when used. The other side of the channel is close by a seal 715 that prevents the liquid product 740 from releasing when aerosol spray can 700 is not in use. The end of the depressible head 705 contains a spring 725 that pushes the head up so that the channel 710 is sealed tight by seal 715. On pressing the depressing head 705, the spring is pushed down, causing the channel 710 to go below the seal 715, thus atomizing the liquid product 740 through the nozzle 720. The aerosol can 700 contains either compressed gas or liquefied gas as propellant 730, which is used to push the liquid product 740 through the tube 735 and out the nozzle 720. The liquid product 740 can be either atomized as a fine mist if propellant 730 is a compressed/liquefied gas or as foam if the propellant 730 is a liquefied gas that causes bubbling in the liquid product. The propellant includes compressed air, inert gases, including nitrous oxide, carbon dioxide, nitrogen; volatile hydrocarbons, including methane, ethane, propane, butane, pentane, their variants and combinations; ethers like dimethyl ether; hydro fluorocarbon. Chlorofluorocarbon will not be generally included due to their ill effects to the environment. The aerosol can 700 may be curved in the bottom 745 for resistance and better utilization of the liquid product 740.

Industry standard method ASTM F1249 for measuring water transmission through films of the invention is used. 1-MCP transmission rates for the films are measured using quasi-isostatic method as described by Lee et al. (Lee, D. S., Yam, K. L., Piergiovanni, L. "Permeation of gas and vapor," *Food Packaging Science and Technoloov*, CRC Press, New York, N.Y., 2008, pp 100-101). Periodically the samples are collected and quantification of 1-MCP is done using gas chromatography (GC) based on the method described by Mir et al., (Nazir A. Mir, Erin Curell, Najma Khan, Melissa Whitaker, and Randolph M. Beaudry. "Harvest maturity, storage temperature and 1-MCP application frequency alter firmness retention and chlorophyll fluorescence of "Redchief Delicious" apples," Journal of American society of horticultural science, 2001, 126(5): 618-624)

Example 1

A two layer film is constructed from polyvinyl alcohol (PVA) comprising about 88% (wt) —OH content) as the outer layer, and an inner layer of spunbonded polyethylene (made from ASPUN™ 6800 series Fiber Grade Resin made by The Dow Chemical Company) is laminated to the outer layer. This 2 layer film structure is then made into a vertical-form-fill-seal (VFFS) package as shown and described for FIG. 2. The package can be used as-is, or it can be filled with a cyclodextrin partially encapsulated 1-methylcyclopropene (1-MCP) ethylene response agent and then sealed in the VFFS apparatus. The package can then be placed into an environment for ultimate release of the partially encapsulated 1-MCP under the proper conditions, e.g., proper moisture or humidity to "activate" the PVA outer film layer and allow the moisture to penetrate the inner film layer of spunbonded PE, thereby dissolving some of the cyclodextrin encapsulant and releasing, in a controlled fashion, the 1-MCP.

Example 2

Tomatoes at near ripe stage are washed, air dried and sliced using Nemco easy tomato slicer (Model 55600-1). Each slice was roughly 3/16" thick. The invention pad containing within 0.5% encapsulated 1-MCP and polyacrylate superabsorbent material is placed on 1 Lb foam tray and over wrapped with a stretchable polyvinyl chloride (PVC) film and held at 10° C. for shelf life evaluations. Similarly another pound of tomato slices are placed on a foam tray that had no pad and over wrapped with a stretchable polyvinyl chloride (PVC) film and held at 10° C. for shelf life evaluations. The shelf life is 10 days for package that had invention pad, whereas the control package without the pad has shelf life of only 5 days. The control package has visible juice which is measured as 100 mL on day 5 of holding at 10° C., in contrast, no visible juice is observed in the package with the invention pad.

Example 3

Tomatoes at near ripe stage are washed, air dried and sliced using Nemco easy tomato slicer (Model 55600-1). Each slice is roughly 3/16" thick. The invention pad containing a mixture of 0.1% encapsulated 1-MCP and 0.1% thymol and polyacrylate superabsorbent material is placed on 1 Lb foam tray and over wrapped with a stretchable polyvinyl chloride (PVC) film and held at 15° C. for shelf life evaluations. Similarly another pound of tomato slices are placed on a foam tray that had no pad and over wrapped with a stretchable polyvinyl chloride (PVC) film and held at 15° C. for shelf life evaluation and mold development. The shelf life is 4 days for package that had invention pad, whereas the control package without the pad has shelf life of only 2 days. The control package has visible mold on day 4 of holding at 15° C., in contrast, no visible mold observed in the package with the invention pad even 3 days past its shelf life, which is day 7 of holding at 15° C.

The invention claimed is:

1. A package for storage and controlled release of a volatile ethylene response manipulation agent, wherein the package consists of a first film layer and a second film layer formed of different material, wherein the first film layer is an inner film layer comprising a volatile ethylene response manipulation agent permeable film structure, and the second film layer is an outer film layer comprising a water soluble polymer.

2. The package of claim 1 wherein the volatile ethylene response manipulation agent is at least partially encapsulated.

3. The package of claim 2 comprising at least 0.1 percent and up to about 10 percent by weight of the volatile ethylene response manipulation agent.

4. The package of claim 1 wherein the volatile ethylene response manipulation agent is cyclopropene, cyclopropene conjugates, cyclopropene salts, or cyclopropene encapsulating materials.

5. The package of claim 1 wherein the package is a sachet or a pad.

6. The package of claim 5, wherein the sachet or pad is placed in a storage, transit or food container such that release of the ethylene response manipulation agent is controlled into an environment.

7. The package of claim 1 wherein the inner film layer comprises perforations.

8. The package of claim 7 wherein the perforations have a mean diameter from 40 micrometers to 900 micrometers.

9. The package of claim 1 wherein the inner film layer comprises microporous film, spun-bonded olefin, waxed paper or non woven nylon or olefin films.

10. The package of claim 1 wherein the outer film layer comprises a coating material with a thickness of 1 to 50 µm.

11. The package of claim 1 wherein the package further stores or contains a polyol liquid medium, or a hydrogel medium, or a combination of polyol and hydrogel medium, wherein the at least one volatile ethylene response manipulation agent is dispersed in the medium.

12. The package of claim 2, wherein the package further stores or contains water absorbing or adsorbing materials.

13. The package of claim 2 wherein the volatile ethylene response manipulation agent is at least partially encapsulated with cyclodextrin.

14. The package of claim 1 wherein the inner film layer has a volatile ethylene response manipulation agent transmission rate, FL-1, at 23° C. of 500 to 250,000 $cm^3/(m^2\text{-day})$.

15. The package of claim 14, wherein the volatile ethylene response manipulation agent is 1-methylcyclopropene.

16. The package of claim 1 wherein the inner film layer has a moisture transmission rate, FL-1, at 37.8° C. of 10 to 500 $cm^3/(m^2\text{-day})$.

17. The package of claim 1, wherein the outer film layer further comprises water absorbing or adsorbing materials.

18. The package of claim 17 wherein the water absorbing or adsorbing materials are polyacrylate based super absorbent polymers, calcium chloride, clay, starch, or silica gel.

19. A multilayer film structure formed into a package for storing and containing a volatile ethylene response manipulation agent and controlling its release into an environment, wherein the multilayer film structure consists of a first film layer and a second film layer housing a partially encapsulated ethylene response manipulation agent, wherein the first film layer and the second film layer are formed of different material, and the second film layer is an outer film layer that is comprising a water soluble polymer, and the first film layer is an inner film layer formed with porosity to allow migration of the volatile ethylene response manipulation agent through the film structure of the package and into an exterior environment.

20. A package for storage and controlled release of a volatile ethylene response manipulation agent, wherein the package consists of a first film layer and a second film layer formed of different material, wherein the first film layer is an inner film layer comprising a volatile ethylene response manipulation agent permeable film structure comprising perforations having a mean diameter from 40 micrometers to 900 micrometers, and the second film layer is an outer film layer comprising a water soluble polymer.

* * * * *